United States Patent [19]

Uno et al.

[11] Patent Number: 4,651,004
[45] Date of Patent: Mar. 17, 1987

[54] OPTICAL GAS DENSITOMETER

[75] Inventors: Masahiro Uno, Hachiooji; Takeo Tanaka, Kunitachi, both of Japan

[73] Assignees: Fuji Electric Corporate Research and Development Co., Ltd.; Fuji Electric Company, Ltd., both of Japan

[21] Appl. No.: 727,416

[22] Filed: Apr. 26, 1985

[30] Foreign Application Priority Data

Apr. 28, 1984 [JP] Japan ................................. 59-87450

[51] Int. Cl.[4] ........................................... G01N21/61
[52] U.S. Cl. .................................... 250/343; 356/439; 356/440
[58] Field of Search ............... 250/343, 351, 352, 353, 250/373, 576, 344, 345, 346; 356/439, 438, 437, 436, 440

[56] References Cited

U.S. PATENT DOCUMENTS

| 3,497,303 | 2/1970 | Enemark et al. | 356/338 |
|---|---|---|---|
| 3,796,887 | 3/1974 | Vincent et al. | 250/565 |
| 4,420,687 | 12/1983 | Martinez et al. | 250/343 |
| 4,549,080 | 10/1985 | Baskins et al. | 250/343 |
| 4,560,873 | 12/1985 | McGowan et al. | 250/339 |

FOREIGN PATENT DOCUMENTS 373545  4/1932  United Kingdom ................ 356/436

OTHER PUBLICATIONS

G. Kivenson, "Some Considerations in the Design of Double-Beam Analyzers for Industrial Control" *Journal of the Optical Society of America* vol. 40, No. 2, (Feb. 1950), pp. 112–118.
"The Energy Expert", Lear Siegler Inc., Environmental Technology Division (Apr. 1982).
Model 3100M Microprocessor Based in situ CO Monitoring System, Dynatron Inc. (May 1982).
Stack Gas and Process Analyzer, Lear Siegler, Inc., Environmental Technology Division (Jan. 1981).

*Primary Examiner*—Janice A. Howell
*Assistant Examiner*—Constantine Hannaher
*Attorney, Agent, or Firm*—Brumbaugh, Graves, Donohue & Raymond

[57] ABSTRACT

An optical gas densitometer is provided comprising a conical filter portion having a front and rear end disposed to the inside of a cell portion and formed into a conical shape, which has a reflection mirror disposed to the inside of the front end thereof, windows disposed at the rear end thereof and in which the angle between an incident optical beam and an exiting optical beam is predetermined. Plate means at the front end of the filter and formed in a space between the inside of the cell portion and the outside of the conical filter portion, divides the space into a gas feed channel below the plate means and a gas exhaust channel above the plate means. An opening channel is disposed between the gas feed channel and the gas exhaust channel towards the rear end of the filter. A partition plate connected to the plate means at the front end of the filter, divides a gas sampling tube into first and second channels which correspond to the feed channel and exhausting channel, respectively.

15 Claims, 5 Drawing Figures

OPTICAL GAS DENSITOMETER

BACKGROUND OF THE INVENTION

The present invention relates to an optical gas densitometer for continuously and rapidly measuring the density of a specific gas by utilizing an absorption band inherent in the infrared wavelength region of that gas molecule.

It is generally desirable that the optical gas densitometer have a high accuracy rate. Three prior optical gas densitometer systems will be explained with reference to FIGS. 3–5 of the accompanying drawings.

FIG. 3 shows a schematic view of a conventional gas analyzer 1 disposed at the outside of a channel 10 of a gas to be measured. The gas analyzer 1 samples the gas from a gas sampling tube 9 inserted in the channel 10, by using suction means, for example, a pump 4. The analyzer 1 carries out pre-treatment such as dehumidification in a drain separator 2, a drain pump 3 and a dehumidifier 5, and the analyzer 1 removes dust or mist in a filter 6. The gas to be measured is then introduced into an analyzer meter 8 for analysis. Reference numeral 7 denotes a sampling gas flowmeter for sampling the measured gas.

This known method, however, is disadvantageous in that there is a substantial delay in time for the meter to actually indicate the density of the gas. This is caused by the extended distance from the sampling point at the gas sampling tube 9 to the gas analyzer 1, the flow rate of the sampled gas, and the pre-treatment and filter section. As a result, this analyzer cannot be put to practical use in a case, for example, of a combustion control in a boiler where fast response is required. Moreover, to reduce the time delay by increasing the suction amount of the sampled gas would only promote maintenance problems such as contaminations in the gas sampling tube 9 or the pre-treatment section.

FIG. 4 shows a schematic structural view of a gas analyzer utilizing a portion of the flow channel of the measured gas as an optical path. An optical source portion 11 and a detection section 12 are oppositely disposed on the diametrical direction of the flow channel 10 of the measured gas, for example flue 10.

This known analyzer, however, has the following defect. It is important but difficult to align the optical axis of the optical source portion 11 with that of the detection section 12. Since the flue 10 generally has a diameter of several meters, a slight dimensional change due to heat distortion or the like in the optical source portion 11 and the detection section 12 may cause a large deviation between their optical axis that would worsen the stability needed for alignment. Further, additional materials are required for installing the optical source portion 11 and the detection section 12. The disposition of a blower is required to prevent the contamination in the light permeating windows for the optical source portion 11 and the detection section 12 in direct contact with the measured gas. Moreover, since it is impossible to fill the flue 10 as the measuring optical path with a standard calibration gas, calibration by the use of the standard calibration gas which is of highest accuracy as the ordinary gage calibration method cannot be employed.

FIG. 5 shows a schematic view of a gas analyzer in which a space between a pipe 14 and a cylindrical filter 15 attached at the top end of the pipe is used as a measuring optical path. A gas analyzer 13 has a front end-closed cylindrical filter 15 attached at the front end of a pipe 14, and a reflection mirror 16 disposed to the inside of the front end of the cylindrical filter 15, in which light is returned by the reflection mirror 16 through a half mirror 17 to introduce a portion of the reflection light to a detector 18. Reference 19 is an optical source, 20 is a chopper for the optical source 19, and 21 is a lens.

This known method, however, is also disadvantageous in that in a flue 10 of a large diameter the ratio of the optical length contributing to the measurement relative to the entire optical length L is small to the case of measuring the gas density at the middle portion of the flue 10. Moreover, the loss of the optical amount is large due to the reflection of the half mirror 17. Another drawback is that the light source 19 requires a large amount of power.

SUMMARY OF THE INVENTION

The present invention has been made to eliminate the foregoing shortcomings. It is an object of the present invention to provide an optical gas densitometer, which requires no pre-treatment for the measured gas, is capable of realizing high speed response, and has satisfactory maintainability and excellent stability.

According to the present invention, a conical filter portion having conical shape with a front end and rear end is disposed in the inside of a cell portion preferably of a cylindrical shape. A reflection mirror is disposed to the inside of the front end of the filter, and light entrance and exit windows are disposed at the rear end of the filter portion. An optical source means provides an incident optical beam through the entrance window, towards the mirror, where it is reflected out through the exit window by the reflection mirror to a detection means. The angle between the incident optical beam and the exit optical beam is made to a predetermined angle. A fork plate, split at the front end of the filter and formed in a space between the inside of the cell portion and the outside of the conical filter portion, divides the space into a gas feed channel below the plate and a gas exhaust channel above the plate. An opening channel is disposed between the gas feed channel and the gas exhaust channel towards the rear end of the filter. A partition plate connected to the fork plate at the top end of the filter divides a gas sampling tube into first and second channels which flow into the feed channel and exhausting channel, respectively. The tube is inserted into a flow channel of a gas to be measured for sampling the gas through the first channel to the feed channel and exhausting the same from the exhaust channel through the second channel. The gas to be measured diffuses through the conical filter portion when gas flows from the gas feed channel to the gas exhaust channel.

BRIEF DESCRIPTION OF THE DRAWINGS

The foregoing, and other objects, features and advantages of the invention will be more clearly understood from the following description taken in conjunction with the accompanying drawings in which.

DETAILED DESCRIPTION OF THE INVENTION

Figure 1:
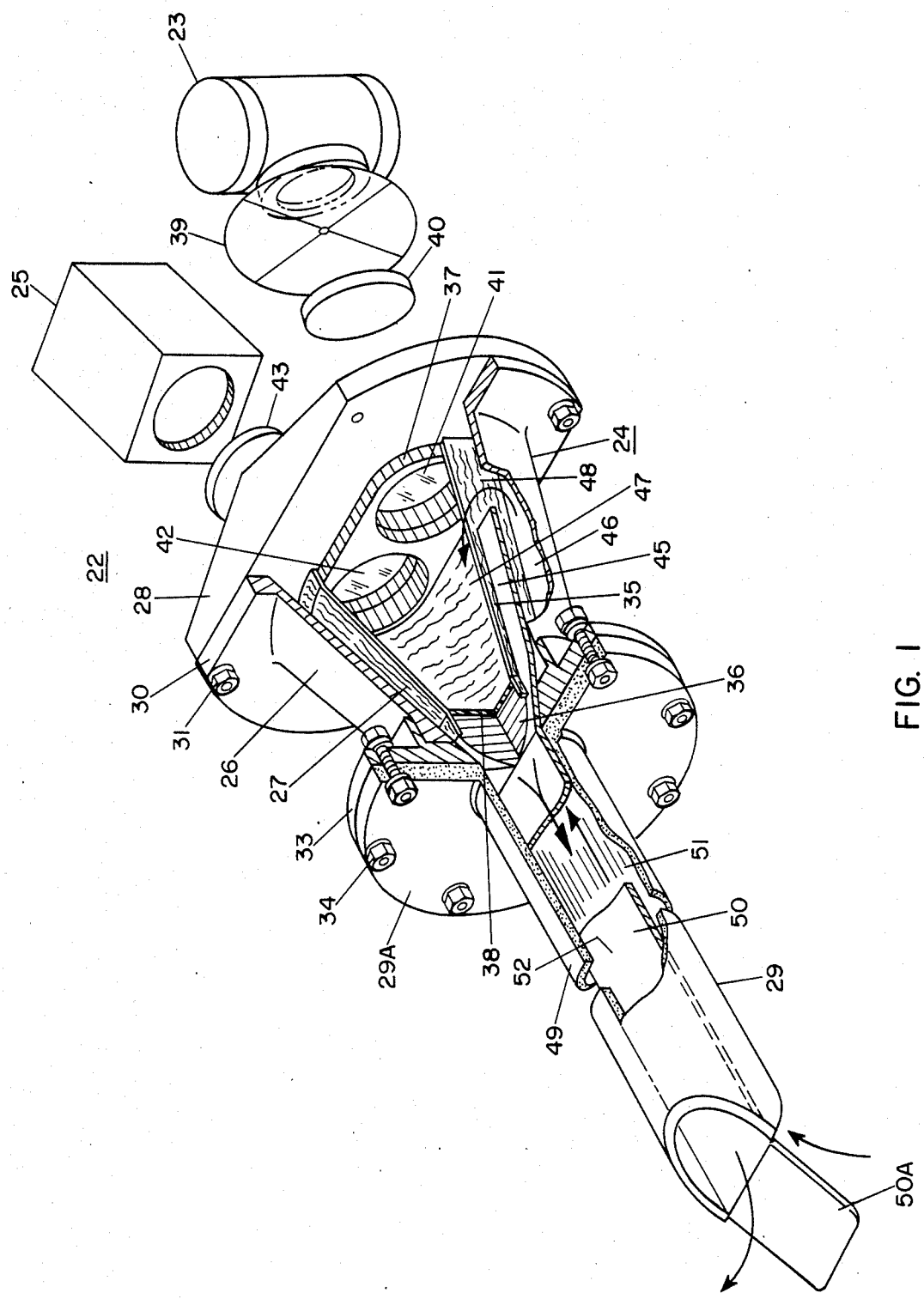
FIG. 1 is a schematic view of the optical gas densitometer in accordance with the present invention.

Referring to the drawings, an optical gas densitometer 22 mainly comprises an optical source portion 23, a cell portion 24, a detection section 25 and a gas sampling tube 29. The cell portion 24 comprises a cell (conical vessel) 26, a conical filter portion 27 contained in the inside of the cell 26 and a holder 28. The cell 26 has a flange 30 secured at one end thereof that is gas-tightly fixed to the holder 28 preferably by means of mounting bolts 31, and a flange 33 secured at the other end thereof that is gas-tightly fixed to a flange 29A of the gas sampling tube 29 preferably by means of mounting bolts 34. The conical filter portion 27 comprises a conical filter 35, a semispherical flow line changing body 36 and an optical beam window 37 disposed to the holder 28 and the like. The conical filter 35 is made of fibers or sintered material and has the semi-spherical flow line changing body 36 inserted at the front leading end thereof and the optical beam window 37 inserted at the rear end thereof such that the respective inserted portion may be kept gas-tight. Further, a reflection mirror 38 is disposed at the inner surface of the flow line changing body 36.

An optical beam radiated from the optical source portion 23 is chopped by a chopper 39, converted into a parallel optical beam through a lens 40 and then entered by way of an entrance window 41 aligned with to the optical beam window portion 37 at the inside rear end of the conical filter 35. The incident optical beam is reflected by the reflection mirror 38, exits from the exiting window 42 as the reflection optical beam and then emits through the lens 43 to the detection section 25. The entrance and exiting windows 41, 42 are gas-tightly disposed to the optical beam window section 37 to prevent the intrusion of external air.

Figure 2:
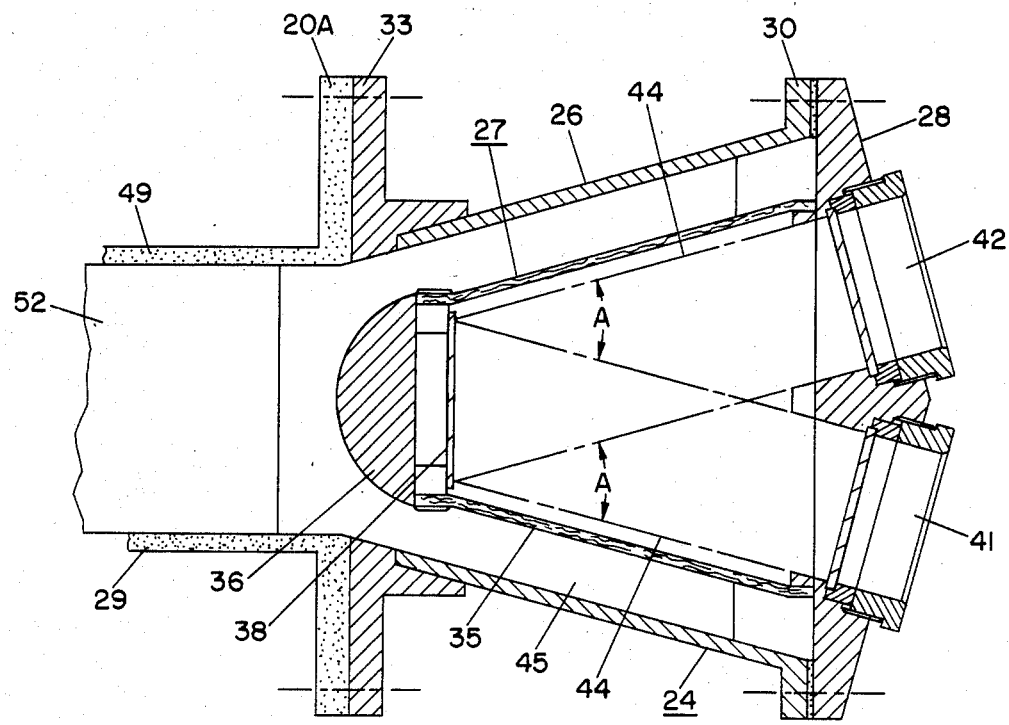
FIG. 2 is a cross-sectional plan view of the optical gas densitometer as illustrated in FIG. 1.

In this case, the gas to be measured diffuses through the conical filter 35 into an optical path 44 comprised of incident and exiting optical beams (FIG. 2). The measured gas absorbs light of a wavelength inherent to the gas to be measured in proportion with the gas density and the length of the optical path 44. The distance between the inner wall of the conical filter 35 reached by the measured gas and the optical path 44 subsequently reached causes a time delay in the measurement. Accordingly, the inner wall of the conical filter 35 is formed to enclose the optical path comprising the incident and the exiting optical beams. Although the angle A between the incident optical beam and the reflection optical beam (FIG. 2) is shown at about 30 degrees in this embodiment, it should be understood that this angle could be as small as about 5 degrees and as large as about 120 degrees.

Further, a fork plate 45, split at the top end of the filter and formed in a space between the inside of the cell 26 and the conical filter portion 27, divides the space into a gas feed channel 46 below the plate and a gas exhaust channel 47 above the plate; an opening channel 48 is disposed between the channels 46 and 47 towards the rear end of the filter. Preferably, the feeding and exhausting channels 46, 47 have generally the same cross-sectional area.

Figure 3:
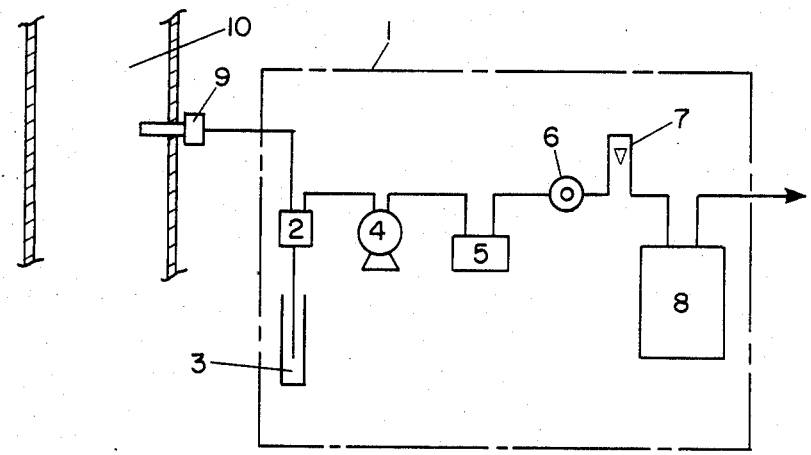
FIG. 3 is a schematic view of one conventional gas analyzer according to the prior art.
Figures 4, 5:
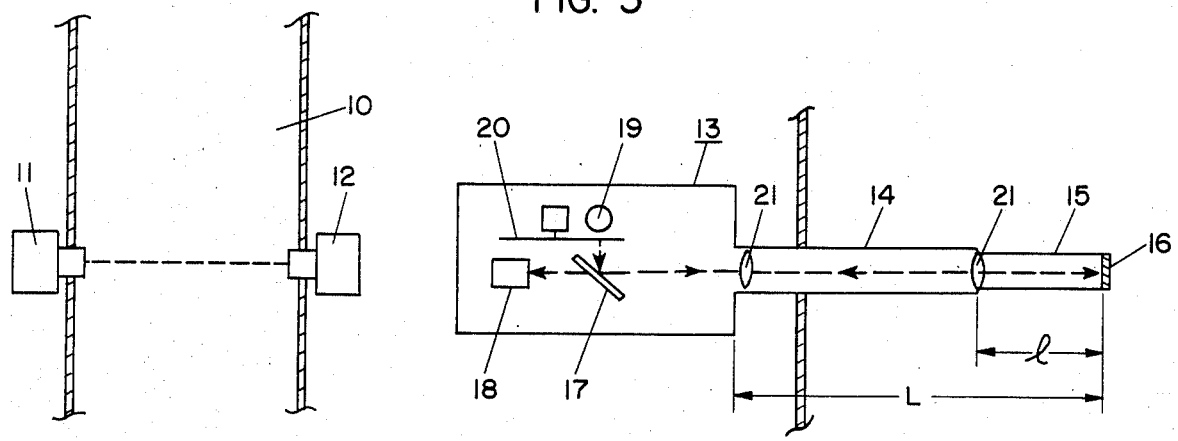
FIG. 4 is a schematic view of another conventional gas analyzer according to the prior art.
FIG. 5 is a schematic view of yet another conventional gas analyzer according to the prior art.

The gas sampling tube 29 has a partition plate 50 disposed to the inside of a cylindrical pipe 49 so as to extend from the fork plate 45. The plate 50 divides the tube 29 into a first channel 51 and a second channel 52. Reference numeral 50A denotes a gas guide plate. The first and the second channels 51 and 52 divided by the partition plate 50 preferably have generally the same cross-sectional area. When the gas sampling tube 29 is inserted into the flow channel 10 of the measured gas (FIG. 3), the measured gas is introduced through the first channel 51 into the gas feed channel 46 and then reversed by way of the opening channel 48 to the gas exhaust channel 47. In the course of flowing through the feeding channel 46 to the exhaust channel 47, the measured gas diffuses through to the inside of the conical filter 35. Further, the measured gas is discharged from the exhaust channel 47 through the second channel 52 to the flow channel 10 of the measured gas. In this case, the gas feed 46 and exhaust channel 47 preferably have generally the same cross-sectional area as the first and the second channels 51, 52 respectively, so that dust will not precipitate or accumulate. Furthermore, the measured gas changes its flow line moderately due to the flow line changing body 36. Accordingly, the flow line changing body 36 need not be restricted only to the semi-spherical shape, but may be conical, for example, as long as it has a shape defining a continuously changing the cross-sectional area so that it functions properly.

The lens 40 disposed on the optical source may be replaced with other optical elements capable of obtaining parallel light such as a parabolic mirror. In the case where the optical beam has a high linearity such a laser beam, lenses 40, 43 on the side of the optical source and the detection section may be omitted.

Furthermore, by using the optical source portion 23 and the detection section 25 exclusively for the infrared, ultra-violet and visible rays to the optical gas densitometer 22, rapid and stable gas density measurement is possible by utilizing absorption of the light of the ingredient to be measured by applying the cell portion 24 and the gas sampling tube 29 in the same manner.

In addition, the diffusing velocity of the measured gas increases as the gas temperature increases. Accordingly, by attaching a heater to the outer wall of the cell 26 or to the outer wall of the conical filter 35, the temperature for the inner wall of the cell 26, the conical filter 35 and the measured gas is increased to exceed the condensation point for the measured gas. This can increase the response speed, as well as prevent the condensation of steams in the measured gas to prevent corrosion or the like in each of the components due to condensation.

Accordingly, various advantages can be obtained in that the problems in the prior art can effectively be solved, pre-treatment for the measured gas is no longer necessary, high speed response is enabled, maintenance troubles can be eliminated and excellent stability is attained.

While there has been described and shown the preferred embodiment of the present invention, it will be recognized by those skilled in the art that various modifications may be made thereto without departing from the spirit of the invention. Accordingly, the invention is to be limited only as defined by the appended claims.

We claim:

1. An optical gas densitometer including an optical source for transmitting an optical beam, and a detection section for receiving said optical beam and for measuring the density of a particular gas, comprising:
   a holding cell portion having front and rear ends;

filter portion means disposed inside said holding cell portion and having front and rear ends corresponding to said front and rear ends of said holding cell;

a gas sampling tube for insertion into a flow channel of the gas to be measured, said tube having one end open to receive gas and a second end attached to the front end of said holding cell;

fork plate means at said front end of said filter portion means for dividing the space between said holding cell and said filter portion means into a gas feed channel below said plate means and a gas exhaust channel above said plate means, said plate means extending substantially from said front end of said filter means to a point short of said rear end of said filter means, such that the area short of said rear end not divided by said plate means forms an open passage between the feed and exhaust channels;

partition plate means disposed inside said gas sampling tube for dividing said tube into a first channel below said partition plate means and a second channel above said partition plate, said partition plate means being aligned with said fork plate means so that said first channel corresponds to said feed channel and said second channel corresponds to said exhaust channel;

window openings situated at the rear end of said filter portion means for allowing said optical beam to enter and to exit said holding cell and the filter portion means; and reflecting means disposed at said front end of said filter portion means for reflecting said optical beam towards said detection system at a predetermined angle;

such that upon inserting said gas sampling tube into a flow channel of the gas, said gas to be measured flows through said first channel, into said feed channel, into said open channel, into said exhaust channel and out said second channel, whereupon the gas which diffuses through said filter portion means into said holding cell affects said optical beam and allows said detection system to measure the density of said gas.

2. The optical gas densitometer of claim 1 wherein said filter portion means comprises:

a flow line changing body located at said front end of said holding cell; and a conical filter diposed inside said holding cell portion.

3. The optical gas densitometer of claim 2 wherein said conical filter is made of fibrous material.

4. The optical gas densitometer of claim 2 wherein said conical filter is of a conical shape to enclose said optical beam in such a manner so that no space exits between said conical filter and said optical beam.

5. The optical gas densitometer of claim 2 wherein said flow line changing body is of a conical shape.

6. The optical gas densitometer of claim 2, further comprising:

a lens; and a chopper, such that said optical source beam is transmitted from said optical source, is chopped by said chopper and is converted into a parallel optical beam through said lens.

7. The optical gas densitometer of claim 6, further comprising a heater to increase the temperature of said gas above the condensation point of said gas.

8. The optical gas densitometer of claim 7 wherein said heater is attached to said holding cell.

9. The optical gas densitometer of claim 7 wherein said heater is attached to said filter portion means.

10. The optical gas densitometer of claim 1 wherein said optical beam comprises an incident optical beam transmitted from said optical source, and a reflection optical beam reflected off said reflection mirror, and wherein said number of windows comprises an entrance window through which said incident optical beam passes, and an exiting window, through which said reflection optical beam passes.

11. The optical gas densitometer of claim 10 wherein the angle between said incident optical beam and said reflection optical beam is at least 5 degrees and no greater than 120 degrees.

12. The optical gas densitometer of claim 11 wherein the angle between said incident optical beam and said reflection optical beam is 30 degrees.

13. The optical gas densitometer of claim 1 wherein said feeding and exhausting channels have the cross-sectional area substantially identical with each other.

14. The optical gas densitometer of claim 13 wherein said first and second channels have the cross-sectional area substantially identical with each other.

15. The densitometer of claim 9 in which the cross-sectional areas of the first and second channels and of the feed and exhaust channels are essentially equal.

* * * * *

UNITED STATES PATENT AND TRADEMARK OFFICE
CERTIFICATE OF CORRECTION

PATENT NO.  : 4,651,004

DATED       : March 17, 1987

INVENTOR(S) : Masahiro Uno et al.

It is certified that error appears in the above-identified patent and that said Letters Patent is hereby corrected as shown below:

Column 6, line 46, "claim 9" should read --claim 14--.

Signed and Sealed this

Thirteenth Day of October, 1987

Attest:

DONALD J. QUIGG

*Attesting Officer*    *Commissioner of Patents and Trademarks*